United States Patent

Lisowsky

[11] Patent Number: 5,708,150
[45] Date of Patent: Jan. 13, 1998

[54] PROCESS FOR PREPARING TRANSITION METAL COMPLEXES CONTAINING DISUBSTITUTED CYCLOPENTADIENYL LIGANDS

[75] Inventor: Richard Lisowsky, Kamen, Germany

[73] Assignee: Witco GmbH, Bergkamen, Germany

[21] Appl. No.: 558,831

[22] Filed: Nov. 15, 1995

[30] Foreign Application Priority Data

Dec. 22, 1994 [DE] Germany .................... 94120380.4

[51] Int. Cl.$^6$ .................... C07F 17/02; C07F 7/00
[52] U.S. Cl. .................... 534/15; 556/1; 556/11; 556/12; 556/43; 556/53; 556/58; 556/143; 556/144; 526/943; 502/103; 502/117
[58] Field of Search .................... 556/11, 12, 43, 556/53, 143, 144, 1, 58; 534/15; 526/943

[56] References Cited

U.S. PATENT DOCUMENTS

| 5,200,537 | 4/1993 | Lee et al. .................... 556/11 |
| 5,336,795 | 8/1994 | Lisowsky .................... 556/56 |

FOREIGN PATENT DOCUMENTS

| 0 620 229 A1 | 3/1994 | European Pat. Off. . |
| 4312270 A1 | 10/1994 | Germany . |

OTHER PUBLICATIONS

Muller, Eugen, Methoden Der Organischen Chemie, Eugen Muller Verlag, 4th Edition, (1970), pp. 660–667.
Chemical Abstracts, vol. 99, No. 19, Nov. 7, 1983, Columbus, Ohio, Abstract No. 157869g.
Chemical Abstracts, vol. 85, No. 23, Dec. 6, 1976, Columbus, Ohio, Abstract No. 176943d.

*Primary Examiner*—Porfirio Nazario-Gonzalez
*Attorney, Agent, or Firm*—Scully, Scott, Murphy & Presser

[57] ABSTRACT

A process for preparing transition metal complexes containing disubstituted cyclopentadienyl ligands of the general formula (1)

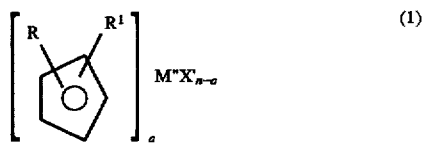

in which a monomeric, monosubstituted cyclopentadiene is reacted using a mixture of an alkali metal oxide or hydroxide and an alkaline earth metal oxide or hydroxide as a metallating agent in polyoxyalkylene polyethers as the reaction medium with organic halides or pseudohalides to give the intermediate disubstituted cyclopentadiene which is, in situ, metallated and reacted with a transition metal halide to give the end product.

12 Claims, No Drawings

PROCESS FOR PREPARING TRANSITION METAL COMPLEXES CONTAINING DISUBSTITUTED CYCLOPENTADIENYL LIGANDS

FIELD OF THE INVENTION

The present invention relates to a process which, starting from monosubstituted cyclopentadienes (RCp), allows for the preparation of transition metal complexes having disubstituted cyclopentadienyl ligands in high yields without isolation of the intermediates, even on an industrial scale.

BACKGROUND OF THE INVENTION

Because of the many possible uses of the above-mentioned transition metal complexes as catalysts in organic synthesis and, in particular, in the polymerization of olefins, the ability to efficiently prepare sandwich complexes disubstituted on the cyclopentadienyl radicals has gained increasing importance industrially.

The synthesis of such compounds is well known in the prior art and is carried out according to the reaction scheme shown in Equations I and II:

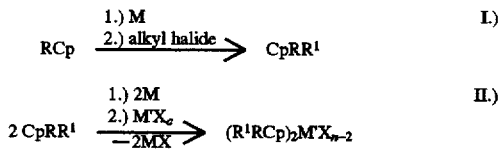

wherein M is a metallating agent such as sodium alkyl, potassium alkyl or lithium alkyl; M' is a transition metal such as Fe, Ti, Zr or Hf; X is Cl, Br, or I; R and $R^1$ are the same or different and are alkyl, cycloalkyl, benzyl, vinyl or allyl radicals; and n is 2–4.

A disadvantage in the prior art synthesis is that the disubstituted cyclopentadiene ($CpRR^1$) is prepared separately before it can be reacted further.

Moreover, the yields of $CpRR^1$ in Equation I are often quite small, so that byproducts have to be removed using complicated procedures before an appropriately pure product for further reaction can be obtained.

The tendency of dialkylcyclopentadienyl compounds to form dimers by an intermolecular Diels-Alder reaction makes the purification complicated, since the monomer, $CpRR^1$, can be obtained in pure form only by multiple distillation and thermal retro-Diels-Alder reaction. However, only these monomers can be used in Equation II of the reaction scheme shown hereinabove. Because of the above-mentioned tendency for dimer formation, the dialkylcyclopentadienyl compounds are not storage stable and they have to be subjected to complicated thermal dedimerization prior to their use. (See Houben-Weyl volume 5/1 c—Methoden der Orgganischen Chemie, Eugen Müller Verlag (Publisher)—fourth edition (1970)—p. 662 ff; George Thieme Verlag, Stuttgart;—Metallocenes: "Chemistry of Organo-Zirconium and—Hafnium Compounds", D. J. Cardin; M. F. Lappert; C. L. Raston; 1986, Ellis Horwood Limited).

Although the yields, according to Equation I, of disubstituted cyclopentadiene derivatives can be improved in some cases, the compounds obtained are either insufficiently pure for the reaction set forth in Equation II or in a solvent which is unsuitable for the reaction described in Equation II and thus has to be removed beforehand. This additional step of removing the solvent may lead to losses in yield and the above-mentioned problems of dimerization.

There is thus particular economical and industrial interest in developing a process which avoids the above disadvantages and makes possible, in a simple reaction procedure, the preparation of metallocenes disubstituted on the cyclopentadiene rings in improved yields, even on a commercial scale.

SUMMARY OF THE INVENTION

It has now been surprisingly discovered that the above-mentioned reactions of monosubstituted cyclopentadienes (RCp) with organic halides give, in high yields and high purity ($\geq 95\%$), correspondingly disubstituted cyclopentadienes ($CpRR^1$), which can be reacted directly, preferably without isolation—and thus without dimerization—to give corresponding metallocenes in high yields and high purity.

This is quite unexpected since it has previously been found that no formation of a disubstituted compound was observed in the reaction of cyclopentadiene with alkyl halides under the same reaction conditions (DE-A-43 12 270).

DETAILED DESCRIPTION OF THE INVENTION

The present invention provides a process for preparing transition metal complexes containing disubstituted cyclopentadienyl ligands of the general formula (1)

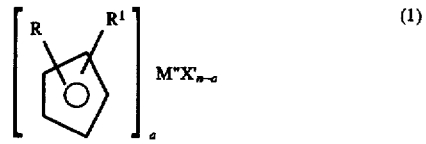

wherein R and $R^1$ are the same or different and each is a $C_1$–$C_{30}$-alkyl group, $C_2$–$C_{30}$-alkenyl group, $C_7$–$C_{30}$-alkylaryl group, $C_8$–$C_{30}$-alkenylaryl group, $C_3$–$C_{12}$-alkoxyalkyl group, $C_1$–$C_{30}$-fluoroalkyl group or an organoelemental radical such as $C_1$–$C_6$-alkyl-tri($C_1$–$C_{10}$-alkyl)silyl; M" is a transition metal such as Fe, V, Cr or Sc, and preferably M" is Ti, Zr or Hf; X' is Cl, Br or I; n is the oxidation state of the transition metal M"; and a is $\leq n$ and is equal to the number of groups X' on the transition metal to be replaced, wherein said process comprises:

(a) reacting, in a first stage a monomeric monosubstituted cyclopentadiene, a first metallating agent and an organic halide in a polyoxyalkylene polyether reaction medium to produce an intermediate disubstituted cyclopentadiene, wherein said metallating agent is a mixture of an alkali metal oxide and/or alkali metal hydroxide and an alkaline earth metal oxide and/or an alkaline earth metal hydroxide; and (b) metallating said intermediate disubstituted cyclopentadiene produced in step (a) with a second metallating agent to produce a metallated product; and (c) reacting said metallated product with a transition metal compound containing a metal from Group IIIB, IVB, VB, VIB or VIII of the Periodic Table of Elements to produce the above-mentioned transition metal complex of formula (1).

The intermediate disubstitued cyclopentadiene formed in step (a) can be subjected directly, in situ, to step (b), or can be isolated from the reaction mixture formed in step (a) and thereafter subjected to step (b).

Preferred substituents R and $R^1$ are branched or unbranched $C_1$–$C_{18}$-alkyl groups, branched or unbranched $C_2$–$C_{18}$-alkenyl groups, $C_3$–$C_6$-alkoxyalkyl groups, $C_1$–$C_3$-alkyl-$C_1$–$C_6$-trialkylsilyl groups, and in particular $C_3$–$C_8$-alkyl groups, and $C_2$–$C_6$-alkenyl groups.

The transition metal used is, preferably, titanium, zirconium or hafnium.

The process of the invention is illustrated below by means of the following reaction scheme (III.):

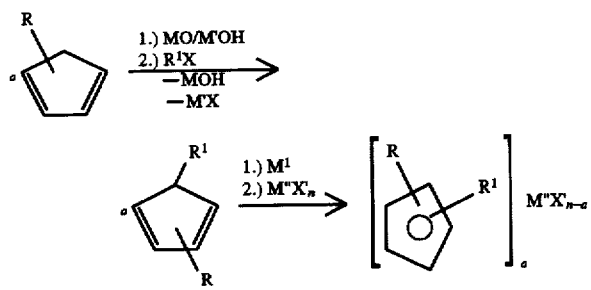

In this scheme: M is an alkali or alkaline earth metal; M' is an alkali or alkaline earth metal; R and $R^1$ are the same or different and each is a $C_1$–$C_{30}$-alkyl group, $C_2$–$C_{30}$-alkenyl group, $C_7$–$C_{30}$-alkylaryl group, $C_8$–$C_{30}$-alkenylaryl group, $C_3$–$C_{12}$-alkoxyalkyl group, $C_1$–$C_{30}$-fluoroalkyl group or an organoelemental radical such as $C_1$–$C_6$-alkyl-tri($C_1$–$C_{10}$-alkyl)silyl; X is a halogen such as Cl, Br or I, or X is —$OSO_2R'$, where R' is alkyl or p-tolyl; $M^1$ is a second metallating agent such as Li, Na, K, NaH, KH, or lithium alkyls; M" is a transition metal such as Fe, V, Cr or Sc, in particular Ti, Zr or Hf; X' is Cl, Br or I; n is the oxidation state of the transition metal M"; and a is ≦n and a is equal to the number of groups X' on the transition metal to be replaced.

In accordance with the instant invention, the mixture of the metal oxide and the metal hydroxide is suspended in glycol diethers. In principle, all combinations of alkali metal and alkaline earth metal oxides and hydroxides are contemplated in the instant invention. By alkali metals is meant especially sodium, potassium and/or lithium. By alkaline earth metals is meant especially magnesium, calcium and barium.

Mixtures of CaO and NaOH, and of MgO and NaOH, in a molar ratio of 1:1 have been found to be particularly useful in the present invention. A further suitable metal oxide employed in the instant invention is BaO.

Based on the particular CpR used, at least one mole of metal oxide/hydroxide is used per mole of CpR. According to the invention, the CpR:MO:MOH ratio is preferably from about 1:1:1 to about 1:3:3, in particular from 1:1.5:1.5 to about 1:2.5:2.5.

Particularly suitable polyoxyalkylene polyethers employed in the present invention are poly(oxyalkylene) glycol ethers, preferably those of the formula $R^2$—O—($CHR^4$—$CH_2$—O)$_n$—$R^3$, where $R^2$ and $R^3$ are each, independently of one another, an alkyl or aryl group, such as phenyl or benzyl, $R^4$ is hydrogen or methyl and n is from about 0 to about 12, preferably n is from about 0 to about 3. The amount of polyoxyalkylene polyether used in the present invention is not critical; however, the lower limit is regarded as an amount in which the reaction mixture is still stirrable.

For metallation using sodium, glycol diethers having $R^2$=$R^3$=ethyl, $R^4$=hydrogen, n=2; $R^2$=$R^3$=methyl, $R^4$=hydrogen, n=2; $R^2$=$R^3$=methyl, $R^4$=hydrogen, n=3 are particularly preferred.

In the case of metallation using lithium alkyls, glycol diethers having $R^2$=$R^3$=methyl, $R^4$=hydrogen, n=1; $R^2$=$R^3$=ethyl, $R^4$=hydrogen, n=1 are additionally particularly preferred.

Monomeric monosubstituted cyclopentadiene and the reagent $R^1$X as the source of the radical $R^1$ to be substituted are then metered in successively.

According to the invention, it is preferred that equimolar amounts of CpR and $R^1$X be employed. If desired, the lower boiling product in each case can be used in an excess of 10–50 mol % to accelerate the reaction.

After the reaction is complete, the sparingly soluble salts formed are separated off and, if necessary, volatile, excess starting materials are removed.

The organic phase can subsequently be used without isolation of the reaction product, with the metallation of the disubstituted cyclopentadiene being carried out by methods known in the art ("Chemistry of Organo-Zirconium and -Hafnium Compounds", D. J. Cardin; M. F. Lappet; C. L. Raston; 1986, Ellis Horwood Limited).

However, if desired, the disubstituted cyclopentadienes (CpRR') can also be isolated from the reaction mixture prior to the metallation.

Particularly suitable metallating agents employed in step (b) of the instant invention are, for example, sodium, sodium hydride and lithium alkyls. The metallation is directly followed by the addition of the transition metal halide.

After separating off the inorganic salts formed, the desired metallocene is isolated and, if desired, further purified by recrystallization.

The raw materials CaO and NaOH are available at low cost and, in comparison with other metallation agents such as sodium or lithium alkyls, are less hazardous to handle.

In the reaction of the instant invention, there is no evidence of overalkylation as is the case, for example, when using elemental sodium or lithium alkyls as metallating agent (see comparative examples).

The alkylation product formed is exclusively the disubstituted cyclopentadiene derivative. In the case of radicals R and $R^1$ which are not too sterically demanding (e.g. linear alkyl groups), this process gives a characteristic isomer mixture of about 3:1 to about 4:1 of 1,2- and 1,3-substituted, for example, dialkylcyclopentadienes, which can be advantageously used as a catalyst component for the polymerization of olefins.

The use of the ethers in the method of the instant invention makes possible both the removal of any traces of low-boiling starting materials still present after the reaction according to Equation I and prior to the reaction according to Equation II, which can further increase the purity of the end product, and also makes possible the direct further metallation and reaction with an appropriate transition metal compound to give the desired metallocene.

If desired, the 1,2-RR$^1$Cp- or the 1,3-RR$^1$Cp-metallocene present in excess can be isolated from the reaction mixture, for example, by recrystallization. In the case of alkyl radicals which are sterically relatively undemanding, for example linear alkyl groups, the 1,2-RR$^1$Cp-metallocenes are formed in excess.

The following examples are given to illustrate the scope of the invention. Because these examples are given for illustrative purposes only, the invention embodied herein should not be limited thereto.

EXAMPLE 1

Preparation of bis(1,2/1,3-methyl-i-propylcyclopentadienyl) zirconium dichloride 10.1 g of CaO and 7.2 g of NaOH, in each case finely powdered, were placed in 60 ml of dimethoxyethane at room temperature and admixed with 9.62 g (0.12 mol) of freshly de-dimerized methylcyclopentadiene.

7.38 g (0.06 mol) of i-propyl bromide was then metered in over a period of about 1 hour, with the temperature being kept below 30° C.

Stirring was continued overnight and the reaction mixture was subsequently analyzed by gas chromatography.

After the i-propyl bromide had been completely reacted, the inorganic salts were filtered off and the filtrate was fractionally distilled.

The fraction of 1,2/1,3-methyl-i-propylcyclopentadiene obtained (6.23 g; 0.051 mol) was placed in dimethoxyethane, admixed at room temperature with 20.4 ml of butyllithium (2.5 molar in hexane; 0.051 mol), refluxed for about 1 hour and then admixed at about 0° C. with 5.94 g (0.0255 mol) of $ZrCl_4$ and stirred for about 1 hour at room temperature.

A LiCl precipitate formed which was separated off. The solvent was then taken off from the filtrate and the residue was recrystallized from pentane.

This gave a 7.26 g yield (70.4%) of an isomer mixture of bis(1,2/1,3-methyl-i-propylcyclopentadienyl)zirconium dichloride.

Zr: (calc.: 22.55) found: 22.40 Cl: (calc.: 17.5) found: 17.35 $^1$H-NMR: (in $CDCl_3$) 6.3–5.8 (m, 6H, Cp ring); 3.1–2.95 (m, 2H, H—C); 2.1–2.3 (m, 6H, $H_3C$); 1.3–0.99 (m, 12H, $H_3C$)

EXAMPLE 2

Preparation of bis(1,2/1,3-methylcyclopentylcyclopentadienyl)zirconium dichloride 10.19 of CaO and 7.2 g of NaOH, in each case finely powdered, were placed in 65 ml of diethylene glycol diethyl ether at room temperature and admixed with 9.62 g (0.12 mol) of freshly de-dimerized methylcyclopentadiene. 8.94 g (0.06 mol) of cyclopentyl bromide were then metered in over a period of about 1 hour, with the temperature being kept below 30° C.

After stirring for about 8 hours at room temperature, excess MeCp was removed by applying a vacuum. Gas chromatographic analysis showed no overalkylation, but only the formation of 1,2/1,3-methylcyclopentylcyclopentadiene.

The reaction mixture was admixed at room temperature with 22 ml of butyllithium (2.5 molar in hexane, 0.055 mol) and refluxed for about 1 hour. After cooling to about 0° C., 6.4 g of $ZrCl_4$ (0.0275 mol) were introduced and the mixture was stirred further for about 1 hour at room temperature.

The mixture was evaporated to dryness in vacuo, the residue was boiled with heptane and filtered hot. After cooling to about −20° C., the product, which had crystallized out, could be isolated by means of filtration and then dried.

This gave 8.4 g (67% yield.) Zr: (calc.: 19.98) found: 19.70 Cl: (calc.: 15.53) found: 15.34 $^1$H-NMR: ($CDCl_3$) 6.35–5.3 mp (m, 6H, Cp); 3.1–2.95 (m, 2H, —CH—); 2.3–2.1 (m, 6H, —CH_); 2.1–1.1 (m, 16H, —$CH_2$)

EXAMPLE 3

Preparation of bis(1,2/1,3-methyloctylcyclopentadienyl) zirconium dichloride

The reaction was carried out using a method similar to Example 2, but 11.58 g of octyl bromide was used in place of the cyclopentyl bromide.

9.1 g of bis(1,2/1,3-methyloctylcyclopentadienyl) zirconium dichloride (yield 61%) was isolated.

Zr: (calc.: 16.74) found: 16.45 Cl: (calc.: 13.02) found: 12.89 $^1$H-NMR: ($CDCl_3$): isomer mixture 6.2–5.9 (m, Cp); 2.5–2.4 (m, 4H, —$CH_2$); [2.2 (s, —$CH_3$, isomer having 1,3-substitution on the Cp); 2.1 (s, —$CH_3$, isomer having 1,2-substitution on the Cp), total: 6H; ratio 3:1 of 1,2-:1,3-substituted]; 1.6–1.2 (m, $(CH_2)_6$—); 0.9–0.8 (dt, —$CH_3$)

EXAMPLE 4

Preparation of bis (1,2/1,3-benzylmethylcyclopentadienyl) zirconium dichloride

The procedure of Example 2 was repeated, but 7.6 g of benzyl chloride was used in place of cyclopentyl bromide. 7.98 g of product (yield 58%) was isolated.

Zr: (calc.: 18.2) found: 18.32 Cl: (calc.: 14.2) found: 14.28 $^1$H-NMR: ($CDCl_3$): 7.3–7.05 (m, 10H, aromatic CH (benzyl)); 6.2–5.7 (m, 6H, Cp); 4.0–3.9 (m, 4H, —$CH_2$—); 2.2–2.05 (m, 6H, —$CH_3$)

EXAMPLE 5

Preparation of bis(1,2/1,3-di-n-butylcyclopentadienyl) zirconium dichloride 48 g of NaOH and 67.3 g of CaO, in each case finely powdered, were placed in 600 ml of diethylene glycol diethyl ether and admixed at room temperature with 59.5 g (0.9 mol) of freshly de-dimerized cyclopentadiene. 82.2 g (0.6 mol) of n-butyl bromide were then metered in at from about 0° C. to about 20° C. After the addition, stirring was continued for about 4 hours at room temperature. The reaction mixture was then filtered, and the filtrate was freed of excess cyclopentadiene by applying a vacuum.

After 60 g of NaOH and 84.1 g of CaO had been introduced into the reaction mixture, 68.5 g (0.5 mol) of n-butyl bromide was metered in at room temperature. The reaction was subsequently allowed to continue for about 8 hours while stirring. Residues of unreacted n-butylcyclopentadiene were removed by applying a vacuum.

The reaction mixture was further admixed at room temperature with 200 ml of butyllithium (2.5 molar in hexane; 0.5 mol). After the addition, the mixture was refluxed for about ½ hour and subsequently cooled to about 0° C. 58.3 g (0.25 mol) of zirconium tetrachloride was then introduced into the reaction mixture at about 0° C.

After a reaction time of about 1 hour, the solvent was removed in vacuo and the residue was taken up in heptane and filtered. The filtrate was cooled to about −30° C. and the solid which precipitated was filtered off and dried.

This gave 89 g (yield: 69% of theory, based on $ZrCl_4$ used) of product.

Zr: (calc.: 17.65) found: 17.60 Cl: (calc.: 13.72) found: 13.65 $^1$H-NMR: ($CDCl_3$): isomer mixture 6.2–5.9 (m, 6H, Cp); 2.7–2.4 (m, 4H, —$CH_2$—): 1.6–1.2 (m, 8H, —$CH_2CH_2$—); 1.0–0.8 (m, 6H, —$CH_3$)

EXAMPLE 6

Preparation of bis(1,2/1,3-methylbutylcyclopentadienyl) zirconium dichloride 17.14 g (214 mmol) of monomeric methylcyclopentadiene was added dropwise at about 10° C. to a mixture of 150 ml of diethyl glycol diethyl ether and 27.5 g of powdered CaO/NaOH. Immediately afterwards, 19.6 g (143 mmol) of n-butyl bromide was metered in. Stirring was continued for about 8 hours at room temperature. The excess methylcyclopentadiene was removed by means of a light vacuum and the inorganic salts which formed were removed by filtration. According to gas chromatography, the yield of n-butylmethylcyclopentadiene was 90%.

No formation of di- or tributylmethylcyclopentadiene was detected.

The clear filtrate was used without further treatment, with the n-butylmethylcyclopentadiene being metallated by addition of n-butyllithium (90% strength in hexane; 114 mmol) and subsequently reacted with $ZrCl_4$ (57 mml; 13.3 g).

After the reaction was complete, all volatile constituents were removed and the residue was admixed with hexane, filtered to separate off the inorganic salts and the filtrate was evaporated. After cooling to about −20° C., the product was crystallized and subsequently isolated by filtration.

After drying in vacuo, this gave 15.5 g (63% of theory) of product which, according to ¹H-NMR, contained 1,2 - and 1,3 -n-butylmethylcyclopentadiene groups in a ratio of about 3:1.

¹H-NMR spectrum (CDCl₃): 6.3–5.93 (m, 6H, —C₅H₃); 2.6–2.4 (m, 4H, —CH₂), 2.2; 2.1 each s, total: 6H, —CH₃ groups of 1,2- and 1,3-substituted cyclopentadienyl groups; ratio 3:1 of 1,2-:1,3-substituted; 1.6–1.3 (m, 8H, —CH₂CH₂); 0.9 (t, 6H, —CH₃) Elemental analysis: Zr: (calc.: 21.09) found: 21.20; Cl: (calc.: 16.39) found: 16.24

EXAMPLE 7

Preparation of bis(1,2/1,3-n-butylmethylcyclopentadienyl) ZrCl₂ with isolation of the n-butylmethylcyclopentadiene A mixture of 64.18 g of CaO and 45.76 of NaOH was placed in 600 ml of dimethoxyethane. 91.66 g (1.44 mol) of freshly de-dimerized methylcyclopentadiene was added at room temperature. 79.98 g of n-butyl bromide (0.572 mol) was subsequently added dropwise over a period of about 1 hour to a maximum temperature of about 30° C.

After about 4 hours, all precipitated salts were removed by means of filtration and, after removal of the solvent, the filtrate was fractionally distilled. This gave, at 30°–45° C./6 mbar, 58.5 g (0.429 mol; 75% of theory, based on n-butyl bromide used) of n-butylmethylcyclopentadiene.

50 g (0.367 mol) of n-butylmethylcyclopentadiene was placed in a mixture of 20 ml of tetrahydrofuran and 180 ml of hexane and admixed dropwise at room temperature with 146.8 ml of butyllithium (2.5 molar in hexane; 0.367 mol). Stirring was continued for about 30 minutes and the mixture was then cooled to about 0° C. At this temperature, 42.8 g of ZrCl₄ (0.184 mol) was introduced into the solution and stirring was continued for about 1 hour at room temperature and for about 2 hours under reflux. The reaction solution was freed of precipitated LiCl and evaporated to dryness.

The residue was taken up in 100 ml of pentane and crystallized at about −50° C.

63.7 g (80% of theory) of product was isolated.

¹H-NMR: identical with that in Example 1. Elemental analysis: Zr: (calc.: 21.09%) found: 21.15; Cl: (calc.: 16.39%) found: 16.30%

EXAMPLE 8

Preparation of bis (1,2/1,3-methylethylcyclopentadienyl) zirconium dichloride 45.76 g of NaOH and 64.16 g of CaO were placed in 600 ml of dimethoxyethane and admixed with 91.66 g of freshly de-dimerized methylcyclopentadiene. Under the conditions indicated in Example 7, 62.33 g of ethyl bromide (0.572 mol) was then added and the reaction was continued. The final fractional distillation for isolating ethylmethylcyclopentadiene gave, at 25°–40° C./150 mbar, 42.2 g (0.39 mol; 68% of theory, based on ethyl bromide used).

40 g of ethylmethylcyclopentadiene (0.37 mol) was placed in 100 ml of tetrahydrofuran and 100 ml of hexane, metallated with 148 ml of butyllithium (2.5 molar in hexane; 0.37 mol) and admixed with 43.1 g of ZrCl₄ (0.185 mol) and worked up under the same reaction conditions as in Example 7.

This gave 53.6 g (77% of theory) of product. Zr: (calc.: 24.23) found: 24.1 Cl: (calc.: 18.83) found: 18.7 ¹H-NMR: 6.2–5.9 (m, 6H, —C₅H₃); 2.6–2.4 (m, 4H, —CH₂—); 2.2; 2.1 each s, total: 6H, —CH₃ groups of 1,2- and 1,3-substituted cyclopentadienyl groups; ratio of 1,2-: 1,3-substituted groups about 3:1; 1.2–1.05 (m (a plurality of superimposed triplets), total: 6H, —CH₃)

COMPARATIVE EXAMPLE

Methylcyclopentadienylsodium with n-butyl bromide
Starting materials used:

0.3 mol of sodium
0.2 mol of methylcyclopentadiene dimer
0.3 mol of n-butyl bromide diethylene glycol diethyl ether The sodium was placed in 200 ml of diethylene glycol diethyl ether and heated to reflux, with the sodium becoming molten and finely dispersed.

The dimeric methylcyclopentadiene was then metered in over a period of about 30 minutes and allowed to react further until the sodium had completely reacted.

The butyl bromide was then metered in at room temperature over a period of about 15 minutes, so that the temperature did not exceed 20° C.

A sample was subsequently taken and analyzed by means of gas chromatography or gas chromatography/mass spectroscopy. About 15% of multiply butylated methylcyclopentadienyl compounds were found.

The above embodiments and examples are given to illustrate the scope and spirit of the present invention. These embodiments and examples will make apparent, to those skilled in the art, other embodiments and examples. These other embodiments and examples are within the contemplation of the present invention; therefore, the instant invention should be limited only by the appended claims.

I claim:

1. A process for preparing a transition metal complex containing disubstituted cyclopentadienyl ligands of the general formula (1)

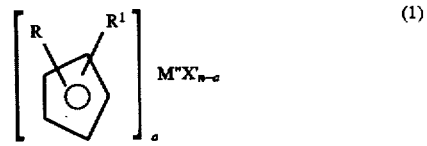

wherein R and R¹ are the same or different and each is a C₁–C₃₀-alkyl group, C₂–C₃₀-alkenyl group, C₇–C₃₀-alkylaryl group, C₈–C₃₀-alkenylaryl group, C₃–C₁₂-alkoxyalkyl group, C₁–C₃₀-fluoroalkyl group or C₁–C₆-alkyl-tri (C₁–C₁₀-alkyl)silyl; M" is a transition metal from Group IIIB, IVB, VB, VIB or VIII of the Periodic Table of Elements; X' is Cl, Br or I; n is the oxidation state of the transition metal M"; a is ≦n; and a is equal to the number of groups X' on the transition metal to be replaced, wherein said process comprises:

(a) reacting a monomeric monosubstituted cyclopentadiene of the formula R—C₅H₉, a first metallating agent and an organic halide R¹-X wherein X denotes a halide, in a polyoxyalkylene polyether reaction medium to produce an intermediate disubstituted cyclopentadiene, wherein said metallating agent is a mixture of one or more alkali metal compounds selected from the group consisting of alkali metal oxides and alkali metal hydroxides and one or more alkaline earth metal compounds selected from the group consisting of alkaline earth metal oxides and alkaline earth metal hydroxides; and (b) metallating said intermediate disubstituted cyclopentadiene produced in step (a) with a second metallating agent selected from the group consisting of Li, Na, K, NaH, KH and lithium alkyls to produce a metallated product; and (c) reacting said metallated product from step (b) with a transition metal compound containing a metal from Group IIIB, IVB, VB, VIB or VIII of the Periodic Table of Elements to produce a transition metal complex of formula (1).

2. The process according to claim 1, wherein the substituents R and R¹ are the same or different and each is a $C_3$–$C_{18}$-alkyl group, $C_2$–$C_{18}$-alkenyl group, $C_3$–$C_6$-alkoxyalkyl group or $C_1$–$C_3$-alkyl-$C_1$–$C_6$-trialkylsilyl group.

3. The process according to claim 2, wherein R and $R^1$ are the same or different and each is a $C_3$–$C_6$-alkyl group or a $C_2$–$C_6$-alkenyl group.

4. A mixture of compounds made by the process of claim 3 comprising a mixture of compounds wherein R and $R^1$ are in the 1,2- and 1,3- positions, wherein the mole ratio of the compounds wherein R and $R^1$ are in the 1,2-position to the compounds wherein R and $R^1$ are in the 1,3-position is 3:1 to 4:1.

5. The process according to claim 1, wherein M" is Fe, V, Cr, Sc, Ti, Zr or Hf.

6. A mixture of compounds made by the process of claim 5 comprising a mixture of compounds wherein R and $R^1$ are in the 1,2- and 1,3- positions, wherein the mole ratio of the compounds wherein R and $R^1$ are in the 1,2-position to the compounds wherein R and $R^1$ are in the 1,3-position is 3:1 to 4:1.

7. The process according to claim 1, wherein M" is Ti, Zr or Hf.

8. The process according to claim 2, wherein M" is Ti, Zr or Hf.

9. The process according to claim 3, wherein M" is Ti, Zr or Hf.

10. The process according to claim 1, wherein said disubstituted cyclopentadiene is isolated prior to step (b).

11. The process according to claim 2, wherein said disubstituted cyclopentadiene is isolated prior to step (b).

12. The process according to claim 3, wherein said disubstituted cyclopentadiene is isolated prior to step (b).

* * * * *

UNITED STATES PATENT AND TRADEMARK OFFICE
CERTIFICATE OF CORRECTION

PATENT NO. : 5,708,150
DATED : January 13, 1998
INVENTOR(S) : Richard Lisowsky

It is certified that error appears in the above-identified patent and that said Letters Patent is hereby corrected as shown below:

Column 5, line 25: "10.19" should read --10.1g--

Column 5, line 49: "$CH_-$" should read --$CH_3$"

Column 9, line 4, Claim 3: "$C_3-C_6$" should read --$C_3-C_8$--

Signed and Sealed this

Twenty-first Day of March, 2000

Attest:

Attesting Officer

Q. TODD DICKINSON

Commissioner of Patents and Trademarks